(12) United States Patent
Nida et al.

(10) Patent No.: US 12,080,398 B2
(45) Date of Patent: Sep. 3, 2024

(54) SYSTEMS AND METHODS FOR HEALTHCARE PROVIDER DASHBOARDS

(71) Applicant: Cambia Health Solutions, Inc., Portland, OR (US)

(72) Inventors: Dean Nida, Portland, OR (US); Michael Brown-Hayes, Portland, OR (US); James Chung, Sherwood, OR (US); Carolyn Espinoza, Woodburn, OR (US); Michael Emerson, Portland, OR (US); John Larson, Portland, OR (US); Jennifer Tschirpke, Portland, OR (US); Stephani Driver, Portland, OR (US); Daniel Jaesup Yoo, Portland, OR (US); Jenifer Curry, Kendrick, ID (US)

(73) Assignee: CAMBIA HEALTH SOLUTIONS, INC., Portland, OR (US)

( * ) Notice: Subject to any disclaimer, the term of this patent is extended or adjusted under 35 U.S.C. 154(b) by 0 days.

(21) Appl. No.: 18/045,427

(22) Filed: Oct. 10, 2022

(65) Prior Publication Data
US 2023/0054513 A1    Feb. 23, 2023

Related U.S. Application Data

(63) Continuation of application No. 16/803,909, filed on Feb. 27, 2020, now Pat. No. 11,501,862.
(Continued)

(51) Int. Cl.
*G16H 10/60* (2018.01)
*G06F 3/0482* (2013.01)
(Continued)

(52) U.S. Cl.
CPC .......... *G16H 15/00* (2018.01); *G06F 3/0482* (2013.01); *G06F 3/04845* (2013.01);
(Continued)

(58) Field of Classification Search
CPC ........ G16H 15/00; G16H 10/60; G16H 40/20; G16H 40/40; G16H 50/30; G16H 80/00;
(Continued)

(56) References Cited

U.S. PATENT DOCUMENTS

| 8,799,010 | B2 | 8/2014 | Kaundinya et al. |
| 9,754,220 | B1 | 9/2017 | Brestoff et al. |

(Continued)

OTHER PUBLICATIONS

Schafer, J. et al., "E-Commerce Recommendation Applications," Data Mining and Knowledge Discovery, vol. 5, No. 1-2, Jan. 2001, 39 pages.
(Continued)

*Primary Examiner* — Maroun P Kanaan
(74) *Attorney, Agent, or Firm* — McCoy Russell LLP

(57) ABSTRACT

Systems and methods for generating dashboards for healthcare providers are provided. In one embodiment, a method comprises receiving, from a user of a client device, a selection of a patient, determining an order of a plurality of display modules, each display module displaying information relating to the patient, generating a dashboard including the plurality of display modules displayed in the order, and transmitting the dashboard to the client device for display to the user. In this way, members may be identified for intervention in a timely manner, and the most relevant information for a healthcare provider may be prioritized for display to a healthcare provider.

20 Claims, 10 Drawing Sheets

Related U.S. Application Data

(60) Provisional application No. 62/848,510, filed on May 15, 2019, provisional application No. 62/812,717, filed on Mar. 1, 2019.

(51) Int. Cl.

| | |
|---|---|
| *G06F 3/04845* | (2022.01) |
| *G06F 3/04847* | (2022.01) |
| *G06N 5/04* | (2023.01) |
| *G06N 20/00* | (2019.01) |
| *G16H 15/00* | (2018.01) |
| *G16H 40/20* | (2018.01) |
| *G16H 40/40* | (2018.01) |
| *G16H 50/30* | (2018.01) |
| *G16H 80/00* | (2018.01) |
| *H04L 67/01* | (2022.01) |

(52) U.S. Cl.
CPC ........... *G06F 3/04847* (2013.01); *G06N 5/04* (2013.01); *G06N 20/00* (2019.01); *G16H 10/60* (2018.01); *G16H 40/20* (2018.01); *G16H 40/40* (2018.01); *G16H 50/30* (2018.01); *G16H 80/00* (2018.01); *H04L 67/01* (2022.05)

(58) Field of Classification Search
CPC ...... G16H 40/63; G16H 50/20; G06F 3/0482; G06F 3/04845; G06F 3/04847; G06N 5/04; G06N 20/00; H04L 67/01; H04L 67/12

See application file for complete search history.

(56) References Cited

U.S. PATENT DOCUMENTS

| | | |
|---|---|---|
| 10,395,762 B1 | 8/2019 | Fram |
| 2014/0039906 A1 | 2/2014 | Wang et al. |
| 2017/0228505 A1 | 8/2017 | Allen et al. |
| 2017/0286622 A1 | 10/2017 | Cox et al. |
| 2020/0279641 A1 | 9/2020 | Nida et al. |
| 2020/0294640 A1* | 9/2020 | Ginsburg ............... G16H 40/20 |

OTHER PUBLICATIONS

Billings, J. et al., "Case findings for patients at risk of readmission to hospital: development of algorithm to identify high risk patients," BMJ, vol. 12, No. 7563, Aug. 12, 2006, Available Online Jun. 30, 2006, 6 pages.

Wennberg, D. et al., "A Randomized Trial of a Telephone Care-Management Strategy," The New England Journal of Medicine, vol. 363, No. 13, Sep. 23, 2010, 11 pages.

Newcomer, S. et al., "Identifying Subgroups of Complex Patients With Cluster Analysis," The American Journal of Managed Care, vol. 17, No. 8, Jul. 31, 2011, 9 pages.

* cited by examiner

SYSTEMS AND METHODS FOR HEALTHCARE PROVIDER DASHBOARDS

CROSS-REFERENCE TO RELATED APPLICATIONS

This is a continuation of U.S. patent application Ser. No. 16/803,909, entitled "SYSTEMS AND METHODS FOR HEALTHCARE PROVIDER DASHBOARDS", and filed on Feb. 27, 2020, which claims the benefit of U.S. Provisional Application No. 62/812,717, entitled "SYSTEMS AND METHODS FOR MANAGEMENT OF CLINICAL QUEUES", and filed on Mar. 1, 2019, and claims the benefit of U.S. Provisional Application No. 62/848,510, entitled "SYSTEMS AND METHODS FOR HEALTHCARE PROVIDER DASHBOARDS", and filed on May 15, 2019. The entire contents of the above-listed applications are hereby incorporated by reference for all purposes.

FIELD

The present description relates generally to intelligent graphical user interfaces or dashboards.

BACKGROUND AND SUMMARY

Healthcare costs are a significant portion of the United States Gross National Product, and continue to rise. A significant portion of these expenses represent costs attributed to individuals who utilize health care services to a higher degree than average. As a minority of healthcare users generate the majority of healthcare costs, predictive modeling of the overall population of healthcare consumers may be effectively used to identify such healthcare users. Customized education and clinical support may then be offered to identified healthcare users to help individuals improve their health and avoid expensive medical events in the future. By proactively monitoring and improving the health of the minority of the population that consumes the majority of healthcare resources, many preventable medical expenses such as hospitalization and emergency room visits may be significantly reduced.

However, despite recent improvements in the ability to perform predictive modeling and risk stratification to identify high-risk individuals, a significant amount of time may pass before a healthcare provider such as a nurse may contact or otherwise intervene with an individual to provide proactive care. In some instances, the individual may undergo hospitalization or suffer from a medical episode before an intervention has occurred.

The inventors have recognized the above issues and have devised several approaches to address them. In particular, systems and methods for generating and actively improving clinical queues are provided. Further, systems and methods for displaying the most actionable and relevant information regarding a patient to a healthcare provider are provided. In one embodiment, a method comprises receiving, from a user of a client device, a selection of a patient, determining an order of a plurality of display modules, each display module displaying information relating to the patient, generating a dashboard including the plurality of display modules displayed in the order, and transmitting the dashboard to the client device for display to the user. In this way, members may be identified for intervention in a timely manner, and the relevant information may be displayed to a healthcare provider in a prioritized manner to provide insights regarding the member.

The above summary is provided to introduce a selection of concepts in a simplified form that are further described below in the Detailed Description. This summary is not intended to identify key features or essential features of the subject matter, nor is it intended to be used to limit the scope of the subject matter. Furthermore, the subject matter is not limited to implementations that solve any or all of the disadvantages noted above or in any part of this disclosure.

DETAILED DESCRIPTION

Figure 2:
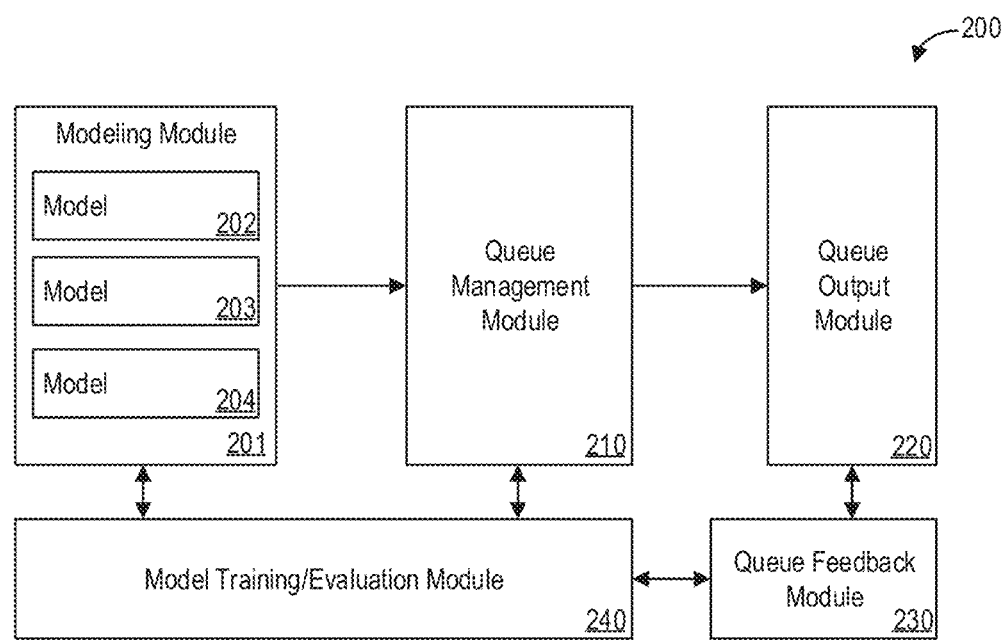
FIG. 2 shows a block schematic diagram illustrating an example architecture for managing clinical queues.
Figure 3:
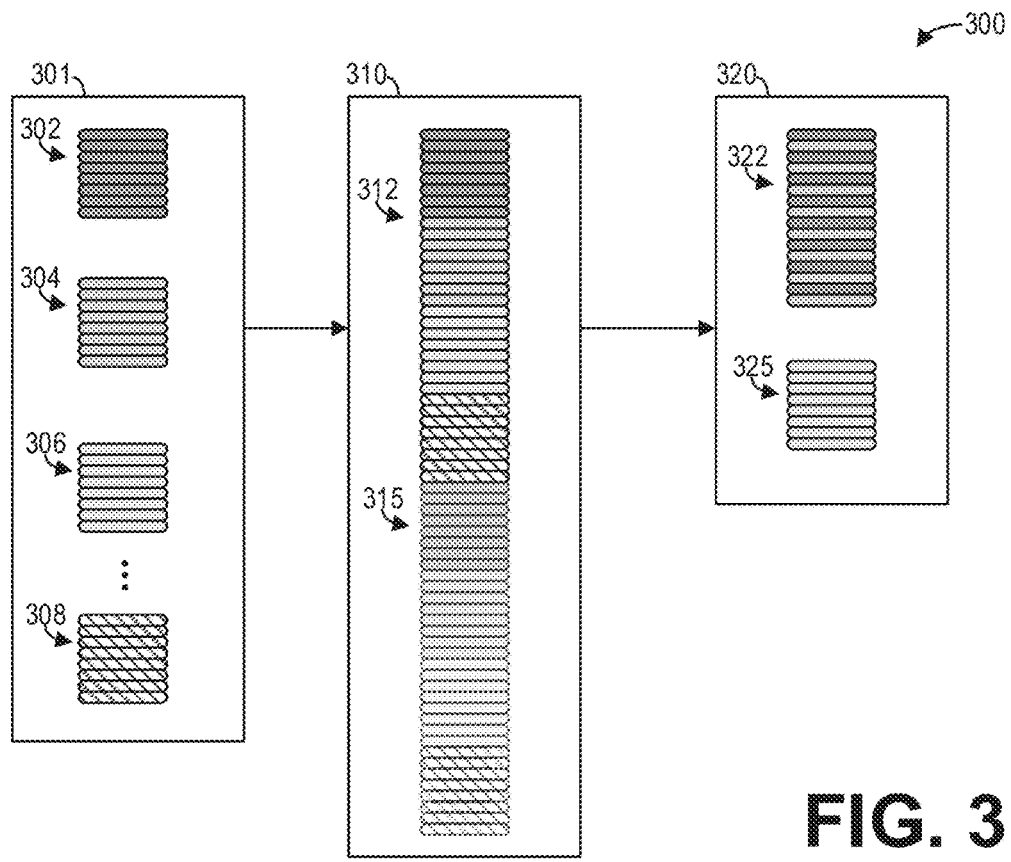
FIG. 3 shows a high-level diagram illustrating an example method for generating clinical queues from a plurality of models.
Figure 4:
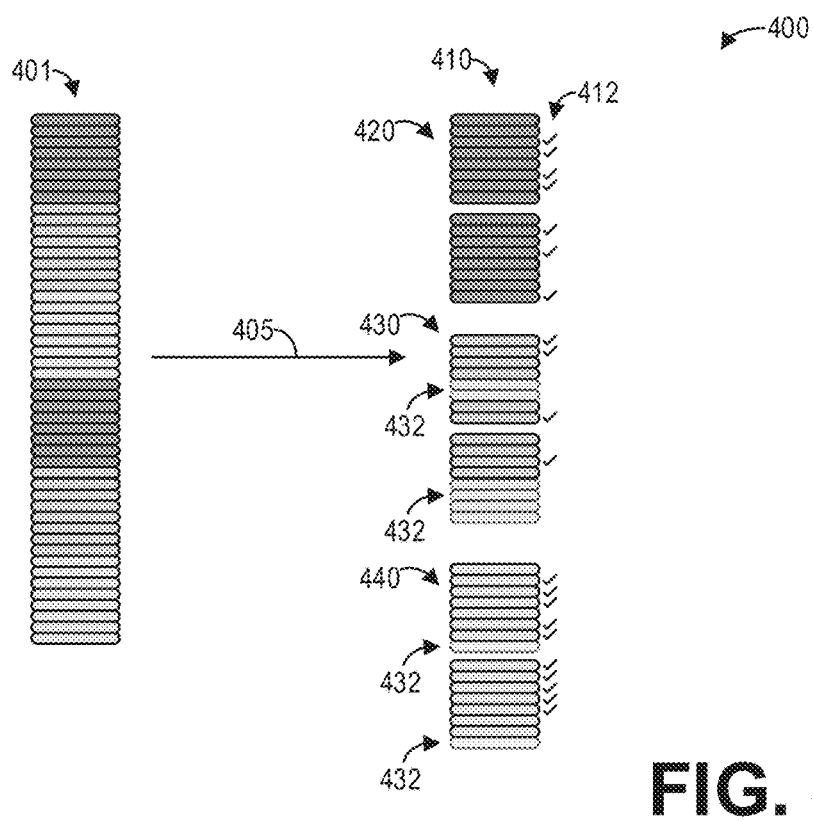
FIG. 4 shows a high-level diagram illustrating an example method for evaluating feedback for clinical queues.
Figure 5:
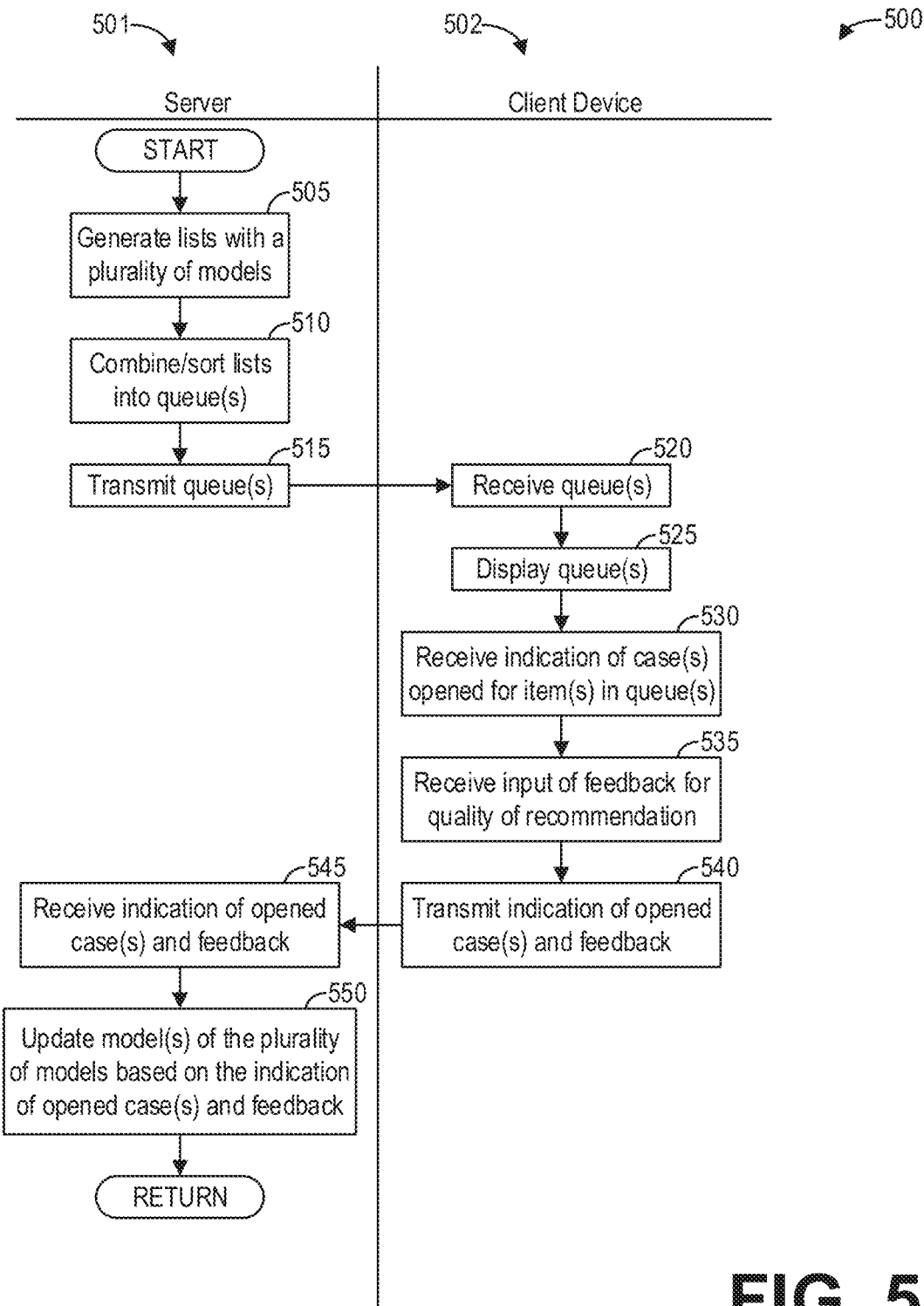
FIG. 5 shows a high-level swimlane flowchart illustrating an example method for active learning for clinical queue management.
Figure 7:
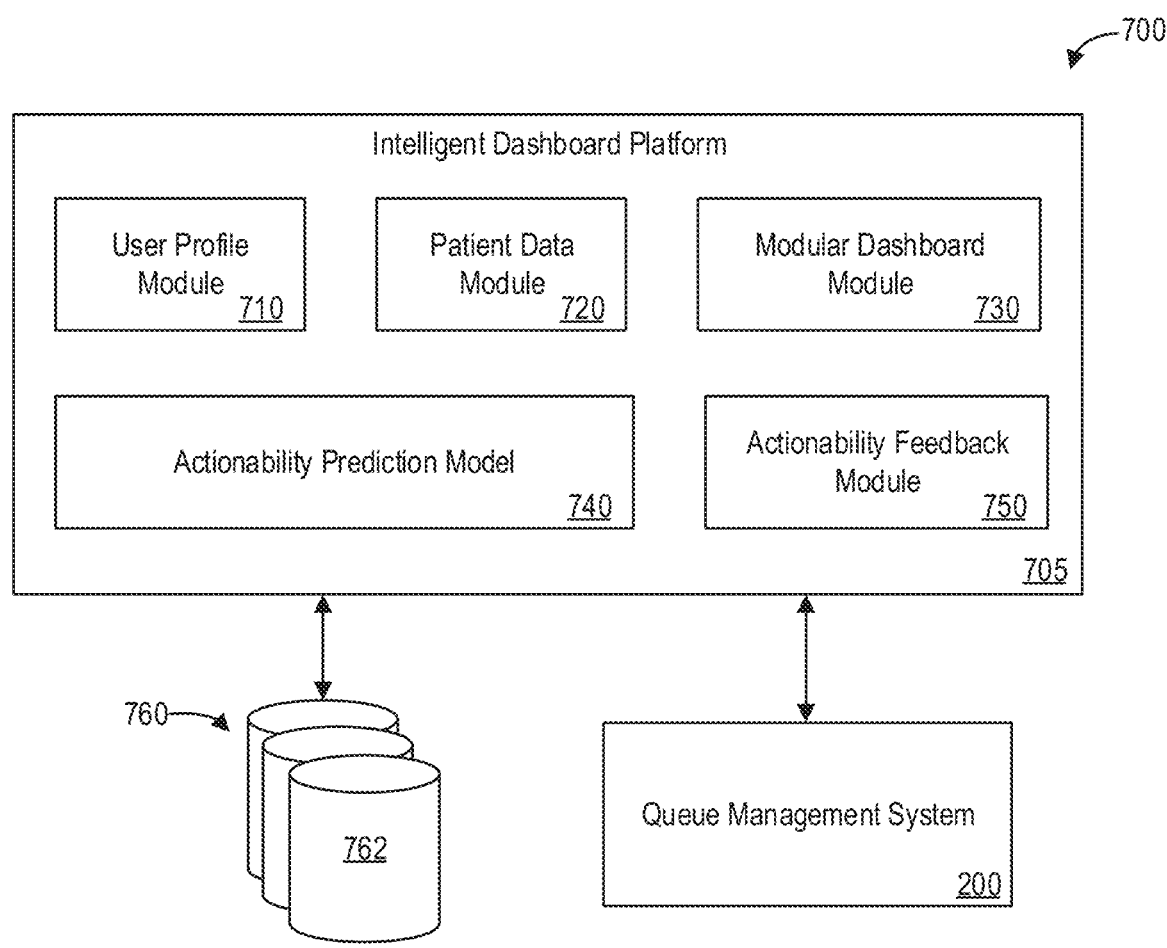
FIG. 7 shows a block schematic diagram illustrating an example architecture for an intelligent dashboard platform.
Figure 8:
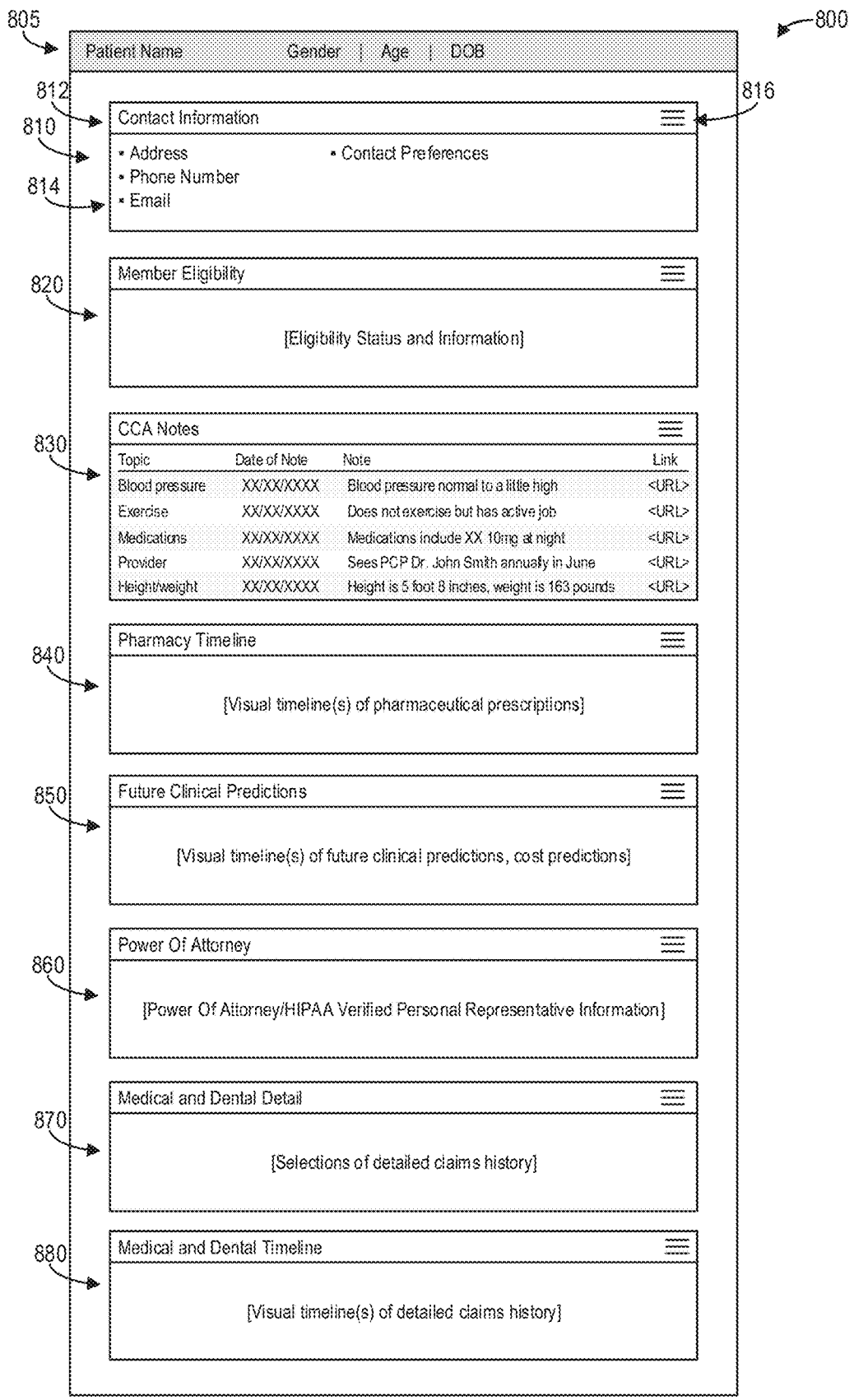
FIG. 8 shows an example graphical user interface including an intelligent dashboard.
Figure 9:
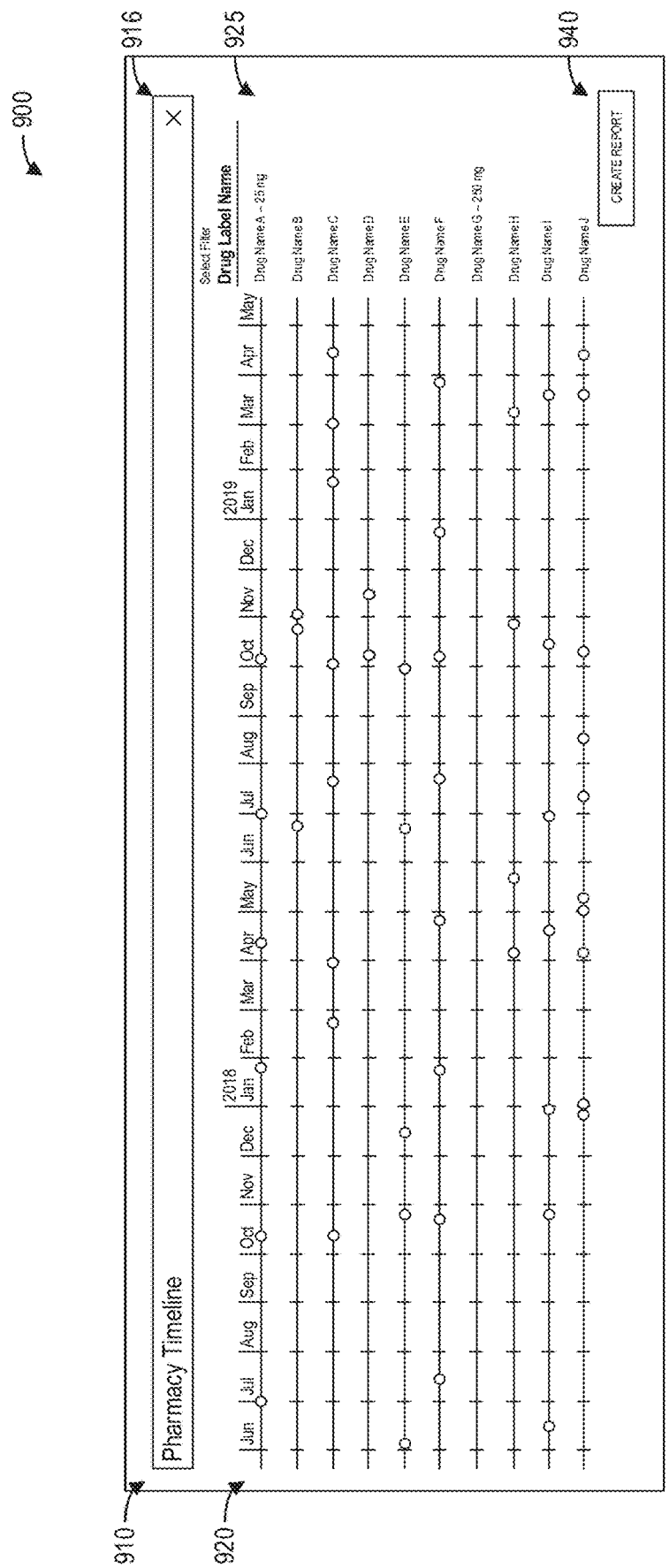
FIG. 9 shows an example display module for depicting a plurality of timelines of pharmaceutical usage.
Figure 10:
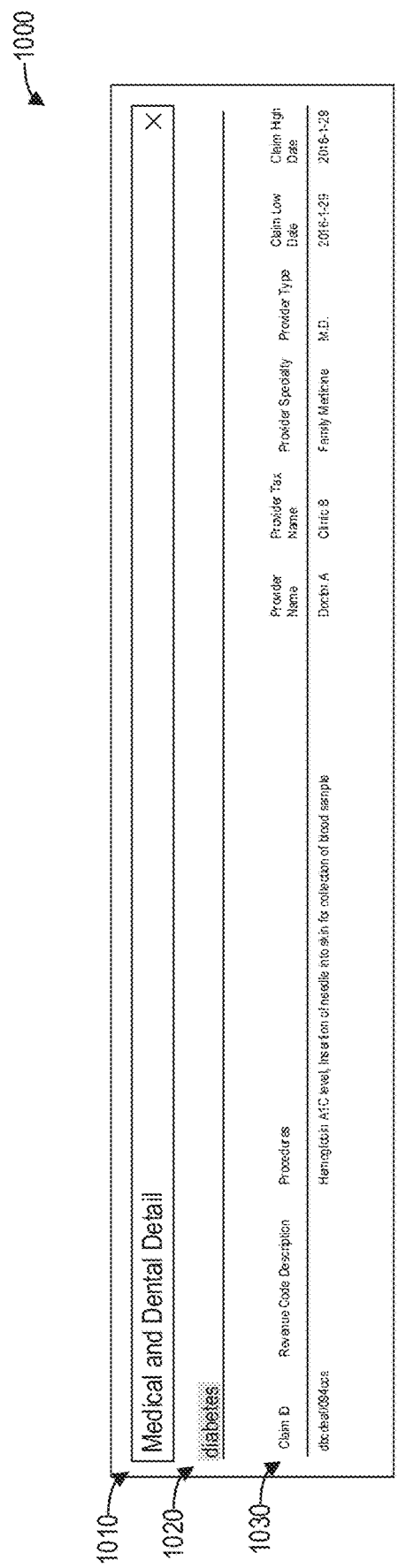
FIG. 10 shows an example display module for depicting medical claim history.
Figure 11:
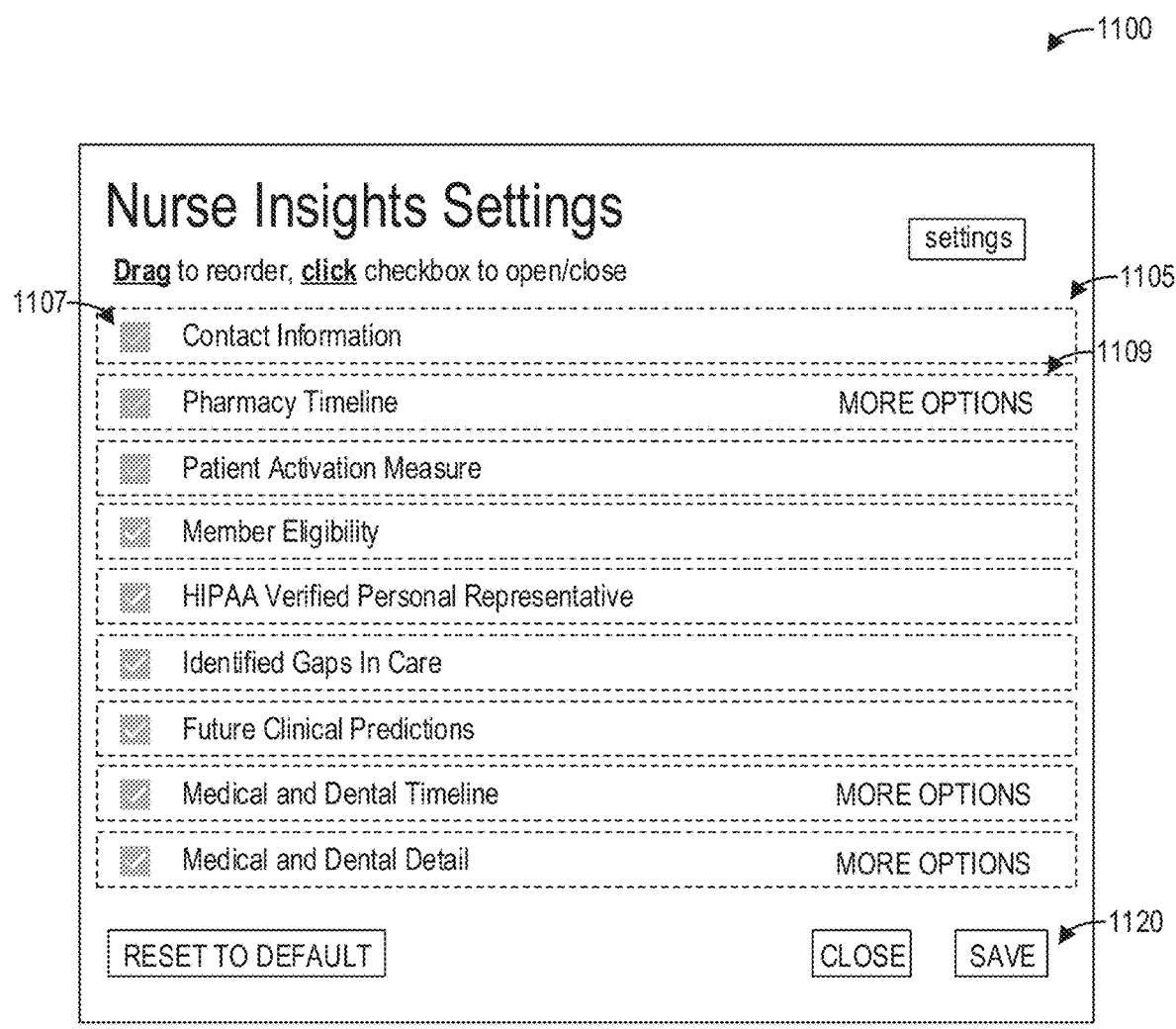
FIG. 11 shows an example graphical user interface for adjusting an intelligent dashboard according to user preferences.

The present description relates to systems and methods for management of clinical queues. In particular, systems and methods are provided for generating clinical queues for use by healthcare providers, such as nurses, comprising a prioritized list of members or individuals for intervention. A computing environment, such as the computer environment or system depicted in FIG. 1, may include a queue management system which provides the healthcare providers with lists of members or patients to contact for a follow-up visit or another intervention. To that end, as depicted in FIG. 2, members are evaluated according to a plurality of different models corresponding to different assessment techniques and assigned scores in a variety of categories, such as risk, cost, potential length of hospitalization, and so on. The queue management system generates sorted lists of members according to these scores, as depicted in FIG. 3, and provides the sorted lists to providers as assignments for contacting or opening cases. A provider provides feedback with regard to the score of a particular member of a given list, as depicted in FIGS. 4 and 5, and the feedback is used to evaluate the efficacy of the assessment technique or predictive model responsive for the score of the particular member. A method for improving a predictive model, such as the method depicted in FIG. 6, includes evaluating the performance of the model before and after incorporating the feedback provided by the healthcare provider to update the model. In this way, providers may give attention to members who need it most, and assessment techniques may be evaluated and improved over time. Intelligent dashboards depicting information for a particular member may be generated by an intelligent dashboard platform, as depicted in FIG. 7. Such a dashboard, as depicted in FIGS. 8-10, provides a healthcare provider with information regarding the member in a plurality of display modules. The order of the display modules may be determined by the intelligent dashboard platform based on preferences of the user, as well as the reasons for including the member in the clinical queue. In this way, the healthcare provider may easily gain insight as to why the member is included in the clinical queue, and make an informed decision for opening a case for the member. The user may adjust display preferences, as depicted in FIG. 11, which may be learned by a predictive model for improving the automated ordering of display modules in the future. A method, such as the method depicted in FIG. 12, for generating a dashboard includes adjusting the order of display modules based on the predictions of patient care, such that the order of display modules prioritizes the patient information that is particularly relevant for review by the healthcare provider.

Figure 1:
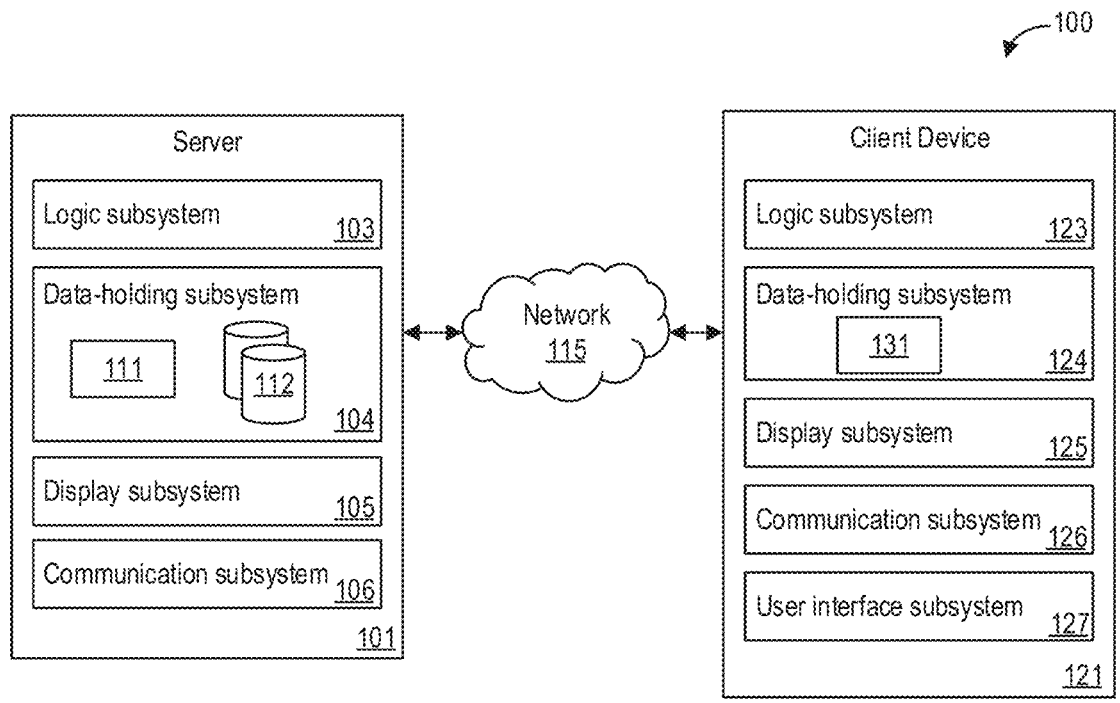
FIG. 1 shows a block schematic diagram of an example computing system for managing clinical queues.

FIG. 1 illustrates an example computing environment 100 in accordance with the current disclosure. In particular, computing environment 100 includes a server 101, a plurality of user devices or client systems including at least one client device 121, and a network 115. However, not all of the components illustrated may be required to practice the invention. Variations in the arrangement and type of the components may be made without departing from the spirit or scope of the invention.

Server 101 may be a computing device configured to generate clinical queues for utilization by one or more healthcare providers. In different embodiments, server 101 may take the form of a mainframe computer, server computer, desktop computer, laptop computer, tablet computer, network computing device, mobile computing device, mobile communication device, and so on.

Server 101 includes a logic subsystem 103 and a data-holding subsystem 104. Server 101 may optionally include a display subsystem 105, communication subsystem 106, and/or other components not shown in FIG. 1. For example, server 101 may also optionally include user input devices such as keyboards, mice, game controllers, cameras, microphones, and/or touch screens.

Logic subsystem 103 may include one or more physical devices configured to execute one or more instructions. For example, logic subsystem 103 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

Logic subsystem 103 may include one or more processors that are configured to execute software instructions. Additionally or alternatively, the logic subsystem 103 may include one or more hardware or firmware logic machines configured to execute hardware or firmware instructions. Processors of the logic subsystem 103 may be single or multi-core, and the programs executed thereon may be configured for parallel or distributed processing. The logic subsystem 103 may optionally include individual components that are distributed throughout two or more devices, which may be remotely located and/or configured for coordinated processing. One or more aspects of the logic subsystem 103 may be virtualized and executed by remotely accessible networked computing devices configured in a cloud computing configuration.

Data-holding subsystem 104 may include one or more physical, non-transitory devices configured to hold data and/or instructions executable by the logic subsystem 103 to implement the herein described methods and processes. When such methods and processes are implemented, the state of data-holding subsystem 104 may be transformed (for example, to hold different data).

In one example, the server 101 includes a queue management system 111 configured as executable instructions in the data-holding subsystem 104. The queue management system 111 may utilize a plurality of models, as described further herein, which predict or otherwise evaluate risk for future healthcare of members. To effectively predict or assess the potential risk of a member, for example, the plurality of models may process one or more healthcare claims associated with the member. To that end, one or more healthcare databases 112 storing one or more medical claims for members may be stored in the data-holding subsystem 104 and accessible to the queue management system 111. In other examples, the one or more healthcare databases 112 may be stored in a separate computing system communicatively coupled to the server 101 and accessible via the network 115.

Data-holding subsystem 104 may include removable media and/or built-in devices. Data-holding subsystem 104 may include optical memory (for example, CD, DVD, HD-DVD, Blu-Ray Disc, etc.), and/or magnetic memory devices (for example, hard drive disk, floppy disk drive, tape drive, MRAM, etc.), and the like. Data-holding subsystem 104 may include devices with one or more of the following characteristics: volatile, nonvolatile, dynamic, static, read/write, read-only, random access, sequential access, location addressable, file addressable, and content addressable. In some embodiments, logic subsystem 103 and data-holding subsystem 104 may be integrated into one or more common devices, such as an application-specific integrated circuit or a system on a chip.

It is to be appreciated that data-holding subsystem 104 includes one or more physical, non-transitory devices. In contrast, in some embodiments aspects of the instructions described herein may be propagated in a transitory fashion by a pure signal (for example, an electromagnetic signal) that is not held by a physical device for at least a finite duration. Furthermore, data and/or other forms of information pertaining to the present disclosure may be propagated by a pure signal.

When included, display subsystem 105 may be used to present a visual representation of data held by data-holding subsystem 104. As the herein described methods and processes change the data held by the data-holding subsystem 104, and thus transform the state of the data-holding subsystem 104, the state of display subsystem 105 may likewise be transformed to visually represent changes in the underlying data. Display subsystem 105 may include one or more display devices utilizing virtually any type of technology. Such display devices may be combined with logic subsystem 103 and/or data-holding subsystem 104 in a shared enclosure, or such display devices may be peripheral display devices.

When included, communication subsystem 106 may be configured to communicatively couple server 101 with one or more other computing devices, such as client device 121. Communication subsystem 106 may include wired and/or wireless communication devices compatible with one or more different communication protocols. As non-limiting examples, communication subsystem 106 may be configured for communication via a wireless telephone network, a wireless local area network, a wired local area network, a wireless wide area network, a wired wide area network, etc. In some embodiments, communication subsystem 106 may allow server 101 to send and/or receive messages to and/or from other devices via a network such as the public Internet. For example, communication subsystem 106 may communicatively couple server 101 with client device 121 via network 115. In some examples, network 115 may be the public Internet. In other examples, network 115 may be regarded as a private network connection and may include, for example, a virtual private network or an encryption or other security mechanism employed over the public Internet.

Further, the server 101 provides a network service that is accessible to a plurality of users through a plurality of client systems such as the client device 121 communicatively coupled to the server 101 via the network 115. As such, computing environment 100 may include one or more devices operated by users, such as client device 121. User device 121 may be any computing device configured to access a network such as network 115, including but not limited to a personal desktop computer, a laptop, a smartphone, a tablet, and the like. While one client device 121 is shown, it should be appreciated that any number of user devices may be communicatively coupled to the server 101 via the network 115.

Client device 121 includes a logic subsystem 123 and a data-holding subsystem 124. Client device 121 may optionally include a display subsystem 125, communication subsystem 126, a user interface subsystem 127, and/or other components not shown in FIG. 1.

Logic subsystem 123 may include one or more physical devices configured to execute one or more instructions. For example, logic subsystem 123 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

Logic subsystem 123 may include one or more processors that are configured to execute software instructions. Additionally or alternatively, the logic subsystem 123 may include one or more hardware or firmware logic machines configured to execute hardware or firmware instructions. Processors of the logic subsystem 123 may be single or multi-core, and the programs executed thereon may be configured for parallel or distributed processing. The logic subsystem 123 may optionally include individual components that are distributed throughout two or more devices, which may be remotely located and/or configured for coordinated processing. One or more aspects of the logic subsystem 123 may be virtualized and executed by remotely accessible networking computing devices configured in a cloud computing configuration.

Data-holding subsystem 124 may include one or more physical, non-transitory devices configured to hold data and/or instructions executable by the logic subsystem 123 to implement the herein described methods and processes. When such methods and processes are implemented, the state of data-holding subsystem 124 may be transformed (for example, to hold different data).

Data-holding subsystem 124 may include removable media and/or built-in devices. Data-holding subsystem 124 may include optical memory (for example, CD, DVD, HD-DVD, Blu-Ray Disc, etc.), and/or magnetic memory devices (for example, hard drive disk, floppy disk drive, tape drive, MRAM, etc.), and the like. Data-holding subsystem 124 may include devices with one or more of the following characteristics: volatile, nonvolatile, dynamic, static, read/write, read-only, random access, sequential access, location addressable, file addressable, and content addressable. In some embodiments, logic subsystem 123 and data-holding subsystem 124 may be integrated into one or more common devices, such as an application-specific integrated circuit or a system on a chip.

When included, display subsystem 125 may be used to present a visual representation of data held by data-holding subsystem 124. As the herein described methods and processes change the data held by the data-holding subsystem 124, and thus transform the state of the data-holding subsystem 124, the state of display subsystem 125 may likewise be transformed to visually represent changes in the underlying data. Display subsystem 125 may include one or more display devices utilizing virtually any type of technology. Such display devices may be combined with logic subsystem 123 and/or data-holding subsystem 124 in a shared enclosure, or such display devices may be peripheral display devices.

In one example, the client device 121 may include executable instructions 131 in the data-holding subsystem 124 that when executed by the logic subsystem 123 cause the logic subsystem 123 to perform various actions as described further herein. As one example, the client device 121 may be configured, via the instructions 131, to receive one or more clinical queues generated and transmitted by the server 101, display the one or more clinical queues via a graphical user interface on the display subsystem 125 to a user such as a healthcare provider, and receive feedback regarding the one or more clinical queues via the user interface subsystem 127.

When included, communication subsystem 126 may be configured to communicatively couple client device 121 with one or more other computing devices, such as server 101. Communication subsystem 126 may include wired and/or wireless communication devices compatible with one or more different communication protocols. As non-limiting examples, communication subsystem 126 may be configured for communication via a wireless telephone network, a wireless local area network, a wired local area network, a wireless wide area network, a wired wide area network, etc. In some embodiments, communication subsystem 126 may allow client device 101 to send and/or receive messages to and/or from other devices, such as server 101, via a network 115 such as the public Internet.

Client device 121 may further include a user input subsystem 127 comprising user input devices such as keyboards, mice, game controllers, cameras, microphones, and/or touch screens. A user of client device 121 may input feedback regarding a clinical queue, for example, via user input subsystem 127. As discussed further herein, client device 121 may stream, via communication subsystem 126, user input received via the user input subsystem 127 to the server 101 over the network 115. In this way, the server 101 may update one or more models for generating clinical queues based on the user input.

Thus server 101 and client device 121 may each represent computing devices which may generally include any device that is configured to perform computation and that is capable of sending and receiving data communications by way of one or more wired and/or wireless communication interfaces. Such devices may be configured to communicate using any of a variety of network protocols. For example, client device 121 may be configured to execute a browser application that employs HTTP to request information from server 101 and then displays the retrieved information to a user on a display such as the display subsystem 125.

FIG. 2 shows an overview of an exemplary arrangement of software modules for a queue management system 200 for generating clinical queues for use by healthcare providers. The queue management system 200 may be implemented, as an illustrative example, as instructions 111 in the data-holding subsystem 104 of a server 101.

The queue management system 200 comprises a modeling module 201 configured with a plurality of models or assessment programs for evaluating or predicting risk of a plurality of individuals. To that end, the modeling module 201 includes a plurality of models including a first model 202, a second model 203, and a third model 204, though it should be appreciated that the modeling module 201 may include more or less than three models in some examples. Specifically, each model of the plurality of models comprises a different model for predicting a variety of measures of healthcare consumption. For example, the plurality of models may be configured to generate scores for individuals based on medical claims data, demographic data, and so on, in a variety of categories such as risk, cost, predicted length of stay, and so on. The output of each model may therefore comprise a list of members with associated scores in a given category. For example, the first model 202 may be configured to predict healthcare costs for each individual based on historical claims data, and so the first model 202 may output a list of members with scores indicating relative predictive healthcare costs. As another example, the second model 203 may be configured to predict a length of stay for each individual, and thus the second model 203 may output a list of members with scores indicating relative predicted lengths of in-patient care. As yet another example, the third model 204 may be configured to predict a risk of a member for future conditions in light of the severity of existing medical conditions, and so the third model 204 may output a list of members with scores indicating relative risk levels. In some examples, the models may segment the individuals according to a threshold score, such that the list outputted by each model excludes individuals with a relatively low score. Thus, in the depicted example, the models of the modeling module 201 comprises a different predictive model configured to predict a different type of score.

Each model of the modeling module 201 may comprise a machine learning model, as an illustrative and non-limiting example. For example, one or more of the models may comprise a machine learning model trained via supervised or unsupervised learning to generate the respective list as discussed hereinabove. To that end, a model of the modeling module 201 may comprise, as a non-limiting and illustrative example, one or more of an artificial neural network, a linear regression model, a logistic regression model, a linear discriminant analysis model, a classification or regression tree model, a naïve Bayes model, a k-nearest neighbors model, a learning vector quantization model, a support vector machine, a random forest model, a boosting model and so on. The models in particular may comprise different types of machine learning models.

The queue management system 200 further comprises a queue management module 210 configured to combine the lists output by the plurality of models of the modeling module 201. For example, the queue management module 210 may combine all of the lists into a master queue which further includes previously identified members or individuals. The queue management module 210 is further configured to generate clinical queues comprising sorted and combined lists of members from the master queue as well as specialized lists of members according to various scores. For example, the queue management module 210 may identify members present on the list of each model output and generate a specialized list including each of the identified members.

To generate the clinical queues, the queue management module 210 may include a machine learning model specifically trained to combine and sort the lists output by the modeling module 201 into the clinical queues. Alternatively, the queue management module 210 may comprise a set of instructions for sorting and combining the master queue into the one or more clinical queues. In order to prioritize the individuals in the plurality of lists, the machine learning model or the sorting protocol of the queue management module 210 may be configured to sort the plurality of individuals in the plurality of lists according to the scores as well as according to the performance of individual models. For example, a model with a higher rate of positive cases may be prioritized over a model with a lower rate of positive cases. Additionally, any arbitrary business logic may be use to prioritize and combine lists. For example, a business user may decide that a high cost model should be prioritized over an inpatient model.

The queue management system 200 further includes a queue output module 220 for outputting the one or more clinical queues generated by the queue management module 210 to one or more client devices, such as a client device 121. In some examples, the queue output module 220 may identify a specific client device 121 for transmitting a particular clinical queue. For example, the queue management module 210 may generate a plurality of clinical queues based at least in part on geographical position, such that separate clinical queues may be provided to different healthcare facilities for servicing local members. Alternatively, the queue management module 210 may generate clinical queues according to healthcare facilities associated with the members. The queue output module 220 may thus specifically transmit an appropriate clinical queue to an appropriate client device 121 associated with a given healthcare provider or healthcare facility. In this way, a healthcare facility will not receive a clinical queue including members who do not receive care at the healthcare facility or have an association with a healthcare provider at the healthcare facility. Further, the queue output module 220 may further distinguish clinical queues for transmission to client devices 121 according to a type of healthcare facility or provider. For example, healthcare providers at a facility specializing in mental health care may prefer clinical queues scored according to different rubrics than healthcare providers at a facility specializing rheumatology. The queue output module 220 may therefore assemble appropriate clinical queues for transmission to appropriate client devices 121 associated with healthcare providers and/or healthcare facilities. Additionally or alternatively, clinical queues may be transmitted to groups of providers and/or facilities based upon financial or partnership agreements.

The queue management system 200 further includes a queue feedback module 230 configured to receive feedback from one or more client devices 121 regarding a clinical queue. The queue feedback module 230 further associates the feedback with the clinical queue, and further may identify the particular model for which the feedback is provided.

The queue management system 200 further includes a model training/evaluation module 240 configured to receive the queue feedback from the queue feedback module 230 and improve one or more models of the modeling module 201 based on the queue feedback. A method for improving one or more models based on feedback is described further herein with regard to FIG. 6. In one example, for each reviewed member, the modeling module 201 may construct a feature vector using patient data (e.g., claims, diagnoses, prescriptions, and so on) obtained from the one or more healthcare databases 112. The feature vector may then be used to predict if an individual has a negative (i.e., not a good case for opening) or a positive (i.e., a good case for opening) label. The model training/evaluation module 240 may utilize the feature vector for an individual along with the feedback, and specifically the indication of whether a case was opened for the individual, to update the model. If the model is evaluated to have a higher precision after training or updating the model with the feedback, the current queueing methodology is replaced with the model. Model performance is thus continuously monitored and models are re-trained or improved as needed.

FIG. 3 shows a high-level diagram illustrating an example method 300 for generating clinical queues from a plurality of models. At 301, a plurality of lists are generated by a respective plurality of models, including a first list 302, a second list 304, a third list 306, and so on up to an nth list 308. A first model, such as the first model 202, may be configured to predict members with high costs, and so the first list 302 may comprise a list of members predicted to use high costs. A second model, such as the second model 203, may be configured to predict whether member will utilize a long length of stay, and so the second list 304 may comprise, for example, a list of members predicted to utilize a long stay. A third model, such as the third model 204, may be configured to predict whether a member is high risk, and so the third list 306 may comprise, for example, a list of members predicted to have high risk.

At 310, the plurality of lists from 301 are compiled into a master queue 312. The master queue 312 further includes a history 315 of all members queued. At 320, one or more queues are output or derived from the master queue 312. For example, select members in the master queue 312 may be sorted and combined into a first queue 322. Further, select members in the master queue 312 may be output into a second queue 324 comprising a specialized list of members. The specialized list of members, for example, may comprise the members identified as high risk in the third list 306.

FIG. 4 shows a high-level diagram illustrating an example method 400 for evaluating feedback for clinical queues. For example, a clinical queue 401 may be provided to a client device such as client device 121 for use by one or more healthcare providers. Feedback 405 regarding the clinical queue 401 may be returned to the server 101, for example. Such feedback 405 may be processed to evaluate the performance of the plurality of models. For example, the master list 401 may be sorted into groups of members according to which model is responsible for a member. For example, a first group 420 of members in the master queue 401, a second group 430 of members in the master queue 401, and a third group 440 of members in the master queue 401 may have been identified respectively by a first model, a second model, and a third model for listing in the master queue 401. The feedback 405 may indicate whether a member was reviewed, and further whether a case was opened for a member in the master queue 401. For example, for illustrative purposes, a plurality of check marks 412 indicating that a case was opened for a given member in the list. Further, as depicted, a shaded entry in a list indicates that the case was not reviewed by a provider, while unshaded entries indicate that the case was reviewed by the provider. Thus, in the depicted example, for the first group 420, all sixteen members were reviewed, and seven cases were opened; for the second group 430, ten of the sixteen members in the second group 430 were reviewed, and four cases were opened for four of the reviewed members; for the third group 440, fourteen of the sixteen members were reviewed, and ten cases were opened for the reviewed members. The opening of a case for a member in the list indicates that the identification of the member and the inclusion of the member was positive. The review of a member without the opening of a case indicates that the inclusion of the member was negative. The absence of a review does not necessarily indicate that the inclusion of the member was negative. In both the instances of a negative inclusion or an unreviewed case, the member may be included in future clinical queues, though a number of negative indications may be identified by the queue feedback module as an indication that the member was incorrectly identified.

FIG. 5 shows a high-level swimlane flowchart illustrating an example method 500 for active learning for clinical queue management. In particular, method 500 relates to the interaction between a server 501, such as the server 101 described hereinabove with regard to FIG. 1, and a client device 502, such as the client device 121. The server 501 may be located remote to the client device 502, which may be associated with a healthcare provider or healthcare facility.

Method 500 begins at 505. At 505, the server 501 generates a plurality of lists with a respective plurality of models. For example, the server 501 may generate the plurality of lists with the modeling module 201. At 510, the server 501 combines and/or sorts the lists into one or more queue(s), for example via the queue management module 210. At 515, the server 501 transmits the one or more queue(s) to the client device 502, for example via the queue output module 220.

At 520, the client device 502 receives the one or more queue(s) from the server 501. At 525, the client device 502 displays at least one of the one or more queue(s) via a display device. A user of the client device 502, such as a nurse, may review the clinical queue(s). Further, a dashboard including information for each member in the clinical queue may be displayed to the user of the client device 502, such that the user may carefully review the medical history of the member and determine whether to open a case and perform an intervention (e.g., contact the member, schedule a visit, and so on).

At 530, the client device 502 receives an indication of one or more case(s) opened for one or more item(s) in the one or more queue(s). Further, at 535, the client device 502 receives an input of feedback for the quality of the recommendation. At 540, the client device 502 transmits the indication of the one or more opened case(s) and the feedback for the quality of the recommendations.

At 545, the server 501 receives the indication of the one or more opened case(s) and the feedback. At 550, the server 501 updates one or more models of the plurality of models based on the indication of the opened case(s) and the feedback. Method 500 then returns.

Figure 6:
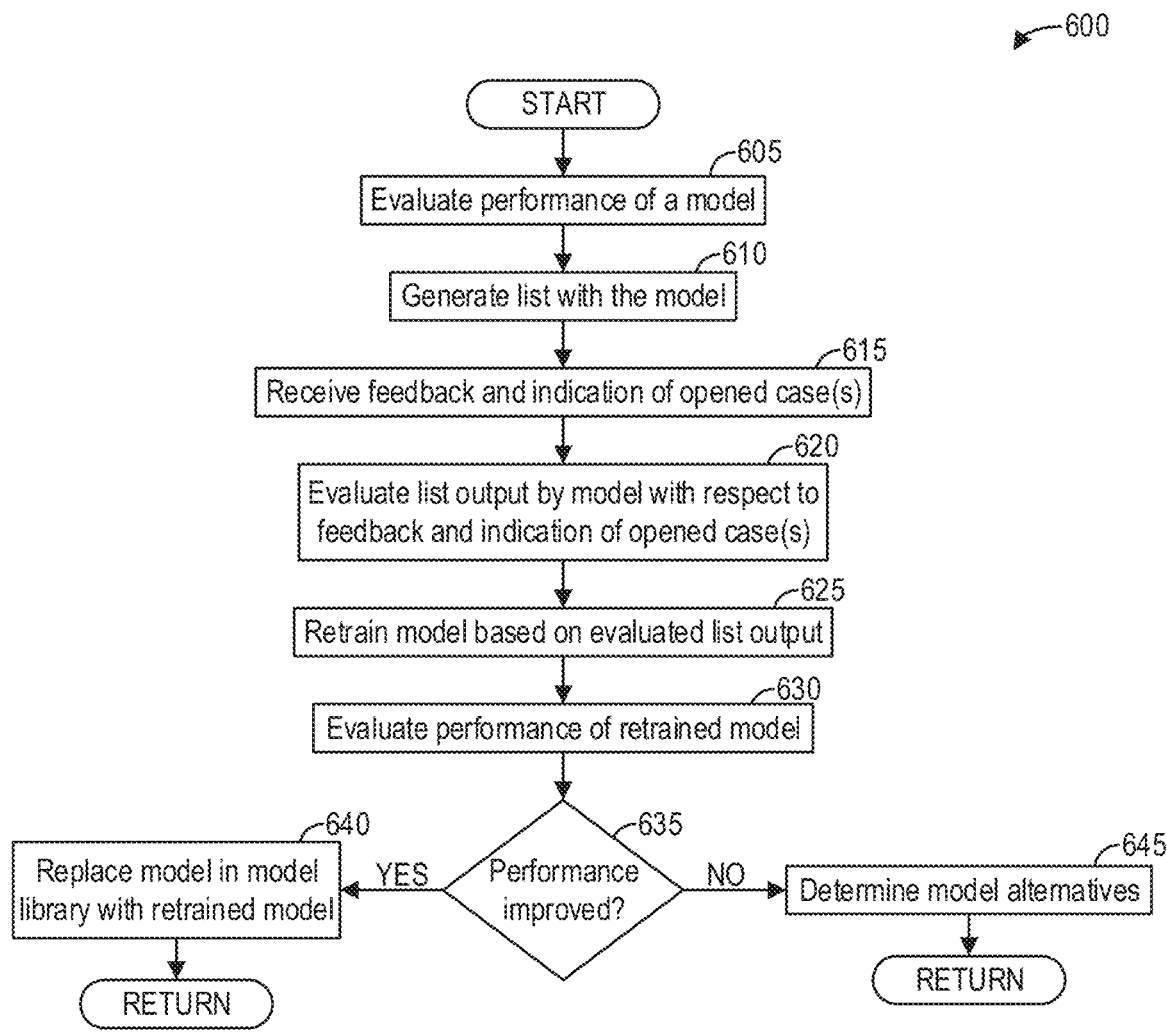
FIG. 6 shows a high-level flow chart illustrating an example method for updating a model for generating a clinical queue.

FIG. 6 shows a high-level flow chart illustrating an example method 600 for updating a model for generating a clinical queue. Method 600 may be carried out by the queue management system 200, for example, and therefore may be implemented as executable instructions 111 in the data-holding subsystem 104 of the server 101.

Method 600 begins at 605. At 605, method 600 evaluates the performance of a model, such as a predictive model in the modeling module 201. The performance of the model may be evaluated based on a training dataset configured for evaluating performance of the model. At 610, method 600 generates a list with the model. The list includes a list of members and scores calculated or generated by the model. The list is incorporated, for example, by the queue management module 210 into the master queue, and at least a portion of the list may be transmitted to a client device 121 as part of a clinical queue for use by a healthcare provider.

At 615, method 600 receives feedback and an indication of opened cases. The feedback may include labels of whether a case was "good" or "bad" and such labels may be used to improve existing models, and for direct prediction of case quality likelihood. Furthermore, the labels of "good/bad case" may be added to a model as an additional prediction task, such that in addition to learning which members are at risk, the model can jointly learn which at-risk members may benefit from an available intervention. At 620, method 600 evaluates list output by model with respect to the feedback and the indication of opened cases. For example, method 600 identifies which feedback and opened cases correspond to the list generated by the model at 610. At 625, method 600 retrains the model based on the evaluated list output. For example, the model may be trained based on the indications of opened cases, such that the model learns that the previous identification of the member was positive, whereas unopened cases are at least partially negative. At 630, method 600 evaluates the performance of the retrained model, for example using the same training dataset used to evaluate performance at 605.

At 635, method 600 determines whether the performance is improved. The performance is improved if the performance of the retrained model evaluated at 630 is higher than the performance of the model evaluated at 605. If the performance is improved ("YES"), method 600 continues to 640. At 640, method 600 replaces the model in the model library with the retrained model. Method 600 then returns.

However, if the performance has not improved ("NO"), method 600 continues to 645. At 645, method 600 determines model alternatives. For example, method 600 may discard the retrained model and continue using the initial model. As another example, method 600 may select another, similar model from the model library for use in generating the clinical queue(s). As yet another example, method 600 may generate an alert that the performance of the model is degrading or insufficient for use in generating the clinical queue(s). Such an alert may be displayed or otherwise presented to a user of the server, for example, to indicate that the model should be investigated or replaced. As another example, a model that is not performing well may be de-prioritized in the queue management system, permanently or temporarily disabled or turned off, or replaced with a more performant identification method as mentioned above. Method 600 then returns.

Thus, case managers conduct a review of each member in the queue. They complete a review form that indicates if the member is a good candidate for case management, as well as an explanation as to why or why not.

Furthermore, when a user is viewing a queue including a list of members automatically selected for inclusion in the queue, the user may select a member in the queue to further review information relating to the member. Responsive to the user selecting the member, the server 101 may output a graphical user interface comprising a dashboard to the client device for display via the display subsystem 125, wherein the dashboard displays information regarding the member retrieved from a plurality of data sources or systems.

FIG. 7 shows a block schematic diagram illustrating an example architecture 700 for an intelligent dashboard platform 705. The intelligent dashboard platform 705 may be implemented, as an illustrative example, as instructions 111 in the data-holding subsystem 104 of the server 101. The intelligent dashboard platform 705 generates an optimized graphical user interface comprising a dashboard including a plurality of display modules, wherein each display module depicts information relating to a patient. The intelligent dashboard platform 705 comprises a user profile module 710, a patient data module 720, a modular dashboard module 730, an actionability prediction model 740, and an actionability feedback module 750.

The user profile module 710 manages and/or stores a plurality of user profiles for either each user with access to dashboards generated by the intelligent dashboard platform 705 or for each type of user who may access dashboards generated by the intelligent dashboard platform 705. For example, a user profile stored in and/or managed by the user profile module 710 for a particular user may include a user name or other identifier for identifying the user, and an indication of a type of user. For example, the indication of the type of user may indicate whether the user is a healthcare provider as well as what type of healthcare provider (e.g., doctor, nurse, and so on), an administrative assistant, an insurance administrator, and so on. In some examples, the display modules included in a dashboard generated by the intelligent dashboard platform 705 may be determined according to the type of user indicated. Further, the order of the display modules displayed in the dashboard may further be determined according to the type of user indicated. In some examples, the user profile may further store personal preferences for the user, such as which display modules to include in a dashboard as well as what order the display modules should be displayed in the dashboard. In this way, the dashboard may be personalized according to the preferences of the user.

The patient data module 720 is configured to determine what type of patient data may be included in the dashboard, and furthermore is configured to populate one or more display modules of the dashboard with patient data. The patient data module 720 further retrieves patient data from one or more databases of a plurality of databases 760, including at least one database 762. One or more of the plurality of databases 760 may be stored locally in the server 101, for example as the databases 112. Additionally or alternatively, one or more of the plurality of databases 760 may be stored in a data system or data server external to the server 101, and so the patient data module 720 may be configured to retrieve patient data from the one or more databases of the plurality of databases 760 from the external data system (not shown) via a network such as the network 115, for example.

The modular dashboard module 730 is configured to populate one or more display modules for a dashboard with data retrieved by and/or stored within the patient data module 720. The modular dashboard module 730 further generates the graphical user interface comprising the dashboard including the one or more display modules populated with the patient data, and outputs the dashboard to the client device 121 for display via the display subsystem 125. The modular dashboard module 730 further adjusts the order of display modules in the dashboard responsive to feedback from the client device 121. In some examples, the modular dashboard module 730 adjusts the order of display modules according to predictions of the actionability of display modules determined by the actionability prediction model 740, as discussed further herein below. Additionally or alternatively, the modular dashboard module 730 may adjust the order of display modules and/or the display of content in the display modules according to predictions of one or more models, such as the model 202, the model 203, or the model 204, in the queue management system 200.

The actionability prediction model 740 is configured to predict the actionability of one or more display modules that may be included in the dashboard. The actionability prediction model 740 may comprise a machine learning model, as an illustrative and non-limiting example. For example, the actionability prediction model may comprise a machine learning model trained via supervised or unsupervised learning to predict the actionability of a display module, or how relevant for display in the dashboard a display module may be, and furthermore may generate an order of display modules in the dashboard according to which display modules may be most relevant to the user viewing the dashboard. To that end, the actionability prediction model 740 may comprise, as a non-limiting and illustrative example, one or more of an artificial neural network, a linear regression model, a logistic regression model, a linear discriminant analysis model, a classification or regression tree model, a naïve Bayes model, a k-nearest neighbors model, a learning vector quantization model, a support vector machine, a random forest model, a boosting model and so on. The actionability prediction model 740 may comprise different types of machine learning models.

The intelligent dashboard platform 705 further includes an actionability feedback module 750 configured to receive feedback from a user regarding the actionability of one or more display modules displayed in the dashboard. The actionability feedback module 750 is further configured to train the actionability prediction model 740 using the actionability feedback, such that the predictions of the actionability prediction model 740 regarding the actionability of one or more display modules improves over time. For example, the actionability feedback module 750 may generate a particular order of display modules for display in the dashboard, and the modular dashboard module 730 may accordingly generate a dashboard displaying the display modules in the particular order. A user may review the dashboard and perform adjustments to the ordering of the display modules, or may provide indications that one or more of the display modules is irrelevant or is particularly relevant to the user. Further, the user may indicate generally that the order of display modules is sufficient or satisfactory, and/or may further rate the actionability of the order overall and/or the actionability of given display modules. The actionability feedback module 750 receives such feedback from the user and trains the actionability prediction model 740 accordingly.

As an example of a dashboard, FIG. 8 shows an example graphical user interface including an intelligent dashboard 800. The intelligent dashboard 800 may be generated, for example, by the intelligent dashboard platform 705, and may be displayed to a user via a display device such as the display subsystem 125 of the client device 121.

The intelligent dashboard 800, also referred to herein simply as a dashboard 800, includes a header 805. The header 805 depicts, as an illustrative and non-limiting example, basic identifying information for the patient such as the patient name and basic patient demographics (for example, gender or sex, age, date of birth, and so on).

The dashboard 800 further includes a plurality of display modules, including a first display module 810, a second display module 820, a third display module 830, a fourth display module 840, a fifth display module 850, a sixth display module 860, a seventh display module 870, and an eighth display module 880. Each display module of the plurality of display modules may include a header identifying the type of display module as well as a body depicting patient information. For example, the first display module 810 includes a header 812 including a title or name of the first display module 810 which indicates the type of information depicted in the first display module 810. The first display module 810 further includes a body section 814 depicting information relating to the patient. As an illustrative example, the first display module 810 is a Contact Information display module, and so the body section 814 depicts contact information for the patient as well as contact preferences.

Further, the display modules may include a hamburger button which allows the user to reorder the display modules as well as view additional settings for the corresponding display module. For example, the first display module 810 includes a hamburger button 816 which may be pressed, clicked, or otherwise selected by the user via the user interface subsystem 127 of the client device 121. While the hamburger button 816 is selected by the user, the user may drag the first display module 810 to another position in the dashboard 800, for example, to re-order the display modules.

As illustrative and non-limiting examples, the second display module 820 depicts Member Eligibility for healthcare services. The third display module 830 depicts notes relating to the patient provided by a healthcare provider. The fourth display module 840 depicts one or more timelines of pharmaceutical prescriptions and usage. As a more detailed example, FIG. 9 shows an example display module 900 for depicting a plurality of timelines of pharmaceutical usage, including the header 910, and the body 820 including a plurality of timelines. The display module 900 further includes a button 916 for removing the display module from the dashboard 800, a filter 925 for filtering the timelines displayed in the display module 900, and a button 940 for automatically generating a report of the data displayed in the display module 900.

The fifth display module 850 depicts one or more visual timeline(s) of future clinical predictions, cost predictions, and so on which may be generated by one or more models in the modeling module 201 described hereinabove. The sixth display module 860 depicts information regarding a person with power of attorney for the patient or a HIPAA verified personal representative, to enable the user of the dashboard 800 to contact an appropriate person for coordinating care for the patient. The seventh display module 870 depicts medical and dental claims history in a textual format, while the eighth display module 880 depicts medical and dental claims history in a visual timeline format. As an illustrative example, FIG. 10 shows an example display module 1000 for depicting medical claim history. The display module 1000 includes a header 1010 as well as a body 1030 depicting medical claims history. The display module 1000 further includes a search bar 1020 which allows the user to search the claims history. Further, the search function may comprise a smart search, wherein metadata and natural language processing and ontologies enable searching for concepts not included in the displayed information. For example, as depicted, a search for "diabetes" returns a blood sugar test even though "diabetes" does not appear in the claim text.

As mentioned above, the order of the display modules in the dashboard 800 may be determined according to preferences of the user of dashboard 800. Additionally or alternatively, the order of the display modules in the dashboard 800 may be determined according to which display modules are most relevant or actionable relative to the condition of the patient. For example, if a model of the modeling module 201 predicts that the patient is at risk due to conflicting prescriptions or a gap in care, the fourth display module 840 depicting the pharmaceutical timelines or the eighth display module 880 depicting the claims history timelines may be displayed near the top of the dashboard 800, while less relevant display modules such as the second display module 820 depicting member eligibility for healthcare coverage may be displayed towards the bottom of the dashboard. As the dashboard 800 may include a large plurality of display modules, not all of the display modules may be depicted simultaneously on the display subsystem 125 of the client device 121. Thus, by selectively ordering the display modules in the dashboard 800, more relevant or actionable display modules may be immediately displayed to the user, while less relevant or actionable display modules may be provided on the dashboard 800 but not necessarily displayed on the display subsystem 125. For example, the user may scroll down the dashboard 800 on the display subsystem 125 to view the less relevant or actionable display modules.

FIG. 11 shows an example graphical user interface 1100 for adjusting an intelligent dashboard according to user preferences. The graphical user interface 1100 depicts an overview of a plurality of display modules 1105 included in a dashboard. The graphical user interface 1100 includes, for each display module 1105, a checkbox 1107 for toggling the display of the display module on or off. For at least some of the display modules 1105, the graphical user interface 1100 further includes buttons 1109 for displaying and adjusting additional options relating to the display modules. After the user adjusts the order and display of the display modules via the graphical user interface 1100, the user may click the save button 1120 to save the adjustments to the order and display of the display modules. The adjustments may be stored in the user profile of the user, and additionally or alternatively may be used to train the actionability prediction model 740 as discussed hereinabove.

Figure 12:
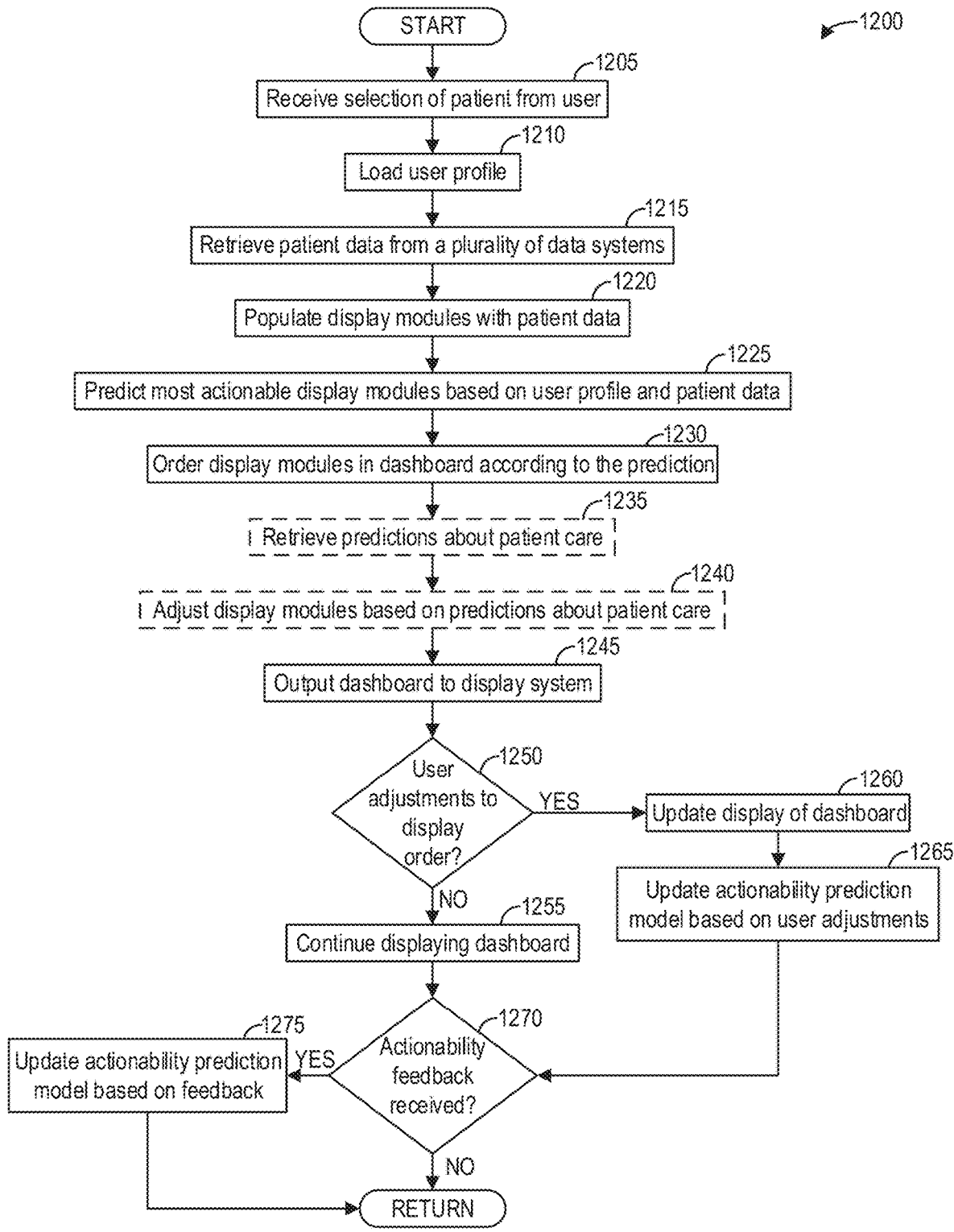
FIG. 12 shows a high-level flow chart illustrating an example method for an intelligent dashboard.

FIG. 12 shows a high-level flow chart illustrating an example method 1200 for an intelligent dashboard. Method 1200 is described with regard to the systems and components of FIGS. 1, 2, and 7, though it should be appreciated that method 1200 may be implemented with other systems and components without departing from the scope of the present disclosure. Method 1200 may be stored as executable instructions in the non-transitory memory of the server 101, for example, and may be executed by a processor thereof to perform the actions described herein.

Method 1200 begins at 1205. At 1205, method 1200 receives a selection of a patient from a user. For example, the user may select, via the user interface subsystem 127, a patient in a clinical queue generated as described hereinabove. At 1210, method 1200 loads a user profile. The user profile comprises a profile of the user, and includes at least an indication of the type of user. The type of user may indicate that the user is a medical doctor (MD), a physician assistant (PA), a certified nursing assistant (CNA), nurse practitioner (NP), doctor of osteopathic medicine (DO), registered nurse (RN), licensed practical nurse (LPN), an administrative assistant, an insurance administrator, and so on. The user profile may further include preferences for display of display modules. For example, a user may consider a given display module particularly irrelevant, and so the user may update their user profile such that the display module is always displayed near the bottom of the dashboard (or not displayed on the dashboard at all). The user may consider another given display module particularly relevant regardless of the context of the patient information, and so the user may update their user profile such that the display module is always displayed or anchored at or at least near the top of the dashboard. In this way, the dashboard display may be personalized for individual users.

Continuing at 1215, method 1200 retrieves patient data from a plurality of data systems. For example, the patient data module 720 may retrieve patient data from one or more databases 760. The patient data may include medical and dental claims, pharmaceutical history, biographical information, provider-generated notes regarding the patient, contact information for the patient, and so on as described hereinabove. The one or more databases 760 may be stored locally or remotely in one or more data storage systems. At 1220, method 1200 populates a plurality of display modules with the patient data. Thus, the plurality of display modules may include information aggregated from a plurality of data systems.

At 1225, method 1200 predicts the most actionable display modules based at least on the user profile and the patient data. For example, method 1200 may predict, with the actionability prediction model 740, which display modules are most relevant or actionable based on the type of user, as well as the patient data. The prediction may comprise a numerical value or quantitative measure of relevance or actionability. As an example of how the actionability or relevancy of a given display module may vary between types of users, a display module depicting quantitative health information (e.g., lab results, pharmaceutical history, and so on) may be more actionable or relevant for a healthcare provider such as a doctor or nurse to view, whereas such a display module may be less actionable or relevant to an administrative assistant or an insurance administrator. In contrast, a display module depicting contact information may be more relevant to the administrative assistant or insurance administrator than to the healthcare provider. Furthermore, the prediction of the actionability or relevance of a display module may be further based on the patient data. For example, the patient data may include an indication of risk due to a lapse in medication without a corresponding interaction with a healthcare provider, which may indicate a need to schedule a follow-up appointment, and so the actionability prediction model 740 may predict that a display module depicting pharmaceutical timelines and a display module depicting provider engagement timelines are more actionable or relevant for display than, say, a display module depicting member eligibility, at least when the dashboard is being generated for a type of user comprising a healthcare provider.

Continuing at 1230, method 1200 orders the display modules in the dashboard according to the prediction. For example, method 1200 may order the display modules in the dashboard in a descending order according to the prediction of actionability, such that the most actionable or relevant display modules are displayed near the top of the dashboard while less actionable or relevant display modules are displayed near the bottom of the dashboard. As discussed hereinabove, each display module included in the dashboard may not be prominently visible on a display system of the client device. For example, display screens are typically limited in size, and so the user may need to scroll or otherwise navigate the dashboard to view all of the display modules in the dashboard. Therefore, the order of the plurality of display modules in the dashboard dictates which display modules are prominently displayed upon initially displaying the dashboard to the user. By ordering the display modules according to the predictions of actionability or relevance, the order of display modules in the dashboard may be prioritized according to the context of the dashboard. That is, as the actionability or relevance is determined based on the type of user as well as the patient data, the order of the display modules is context dependent.

At 1235, method 1200 optionally retrieves predictions about patient care. For example, method 1200 may retrieve predictions about the patient care from the queue management system 200, and more specifically from one or more models of the modeling module 201. As these predictions about patient care are responsible for the inclusion of the patient in the clinical queue displayed to the user, the predictions may be especially relevant to ordering the display modules in the dashboard. Thus, at 1240, method 1200 optionally adjusts the display modules based on the predictions about patient care. For example, if the model 306 of the modeling module 201 predicts a high risk for the patient such that the patient is included in a clinical queue, method 1200 may adjust the order of display modules to emphasize aspects of the patient data relating to the prediction for high risk. For example, if the models predict a high cost or long length of stay of a patient due to a particular medical condition (e.g., pregnancy or a terminal illness), method 1200 may adjust the display of the medical claims history to emphasize or highlight claims relating to the particular medical condition, while also re-ordering the display modules such that the display module including the medical claims history is displayed near the top of the dashboard. In this way, the user may be able to immediately ascertain the current condition or state of the patient when viewing the dashboard, rather than having to scroll through the display modules and carefully examine the information potentially included or even potentially excluded therein.

After ordering the display modules in the dashboard according to the type of user, the patient data, and the predictions about patient care, method 1200 continues to 1245. At 1245, method 1200 outputs the dashboard to a display system, such as the display subsystem 125, for display to the user. Thus, by simply selecting the patient from the clinical queue, the user is provided with a dashboard which automatically prioritizes information regarding the patient that is of particular actionability or relevance to the user.

At 1250, method 1200 determines whether user adjustments to the display order are received. For example, method 1200 may receive user adjustments to the display order if the user drags and drops or otherwise re-organizes the order of display modules in the dashboard. If user adjustments are not received ("NO"), method 1200 continues to 1255, wherein method 1200 continues displaying the dashboard as-is.

However, if user adjustments to the display order are received ("YES"), method 1200 proceeds from 1250 to 1260. At 1260, method 1200 updates the display of the dashboard based on the user adjustments to the display order. Further, at 1265, method 1200 updates the actionability prediction model based on the user adjustments. Method 1200 may further update the user profile of the user with the user adjustments, such that the user profile stores at least the preferred display order of the display modules for the given patient. In this way, if the user subsequently selects the patient for review via the dashboard, the order of the display modules may reflect the user adjustments received at 1250. Further, the actionability prediction model improves over time, such that predictions of actionability or relevance are improved, responsive to user adjustments without the user having to provide explicit feedback for the model.

Method 1200 proceeds from 1255 or 1265 to 1270. At 1270, method 1200 determines whether actionability feedback is received. Method 1200 receives actionability feedback if the user inputs, via the user interface subsystem 127 for example, ratings of actionability or relevance for one or more of the display modules. For example, the dashboard may include a feature for providing such feedback, which may include a numerical rating system or a checkbox for indicating the actionability or relevance of a particular display module, or the order of display modules in general. Thus, the user may provide explicit feedback regarding the actionability or relevance of one or more display modules in the dashboard. If actionability feedback is not received ("NO"), method 1200 returns. However, if actionability feedback is received ("YES"), method 1200 continues to 1275. At 1275, method 1200 updates the actionability prediction model based on the feedback. Method 1200 then returns.

Thus, systems and methods for intelligent dashboards for healthcare providers are provided. In one embodiment, a method comprises receiving, from a user of a client device, a selection of a patient, determining an order of a plurality of display modules, each display module displaying information relating to the patient, generating a dashboard including the plurality of display modules displayed in the order, and transmitting the dashboard to the client device for display to the user.

In a first example of the method, determining the order of the plurality of display modules comprises predicting, for each display module of the plurality of display modules, an actionability or relevancy of each display module for display to the user, and determining the order according to the predicted actionability or relevancy. In a second example of the method optionally including the first example, the order of the plurality of display modules is determined based on a type of user for the user. In a third example of the method optionally including one or more of the first and second examples, the order of the plurality of display modules is determined according to one or more healthcare predictions for the patient. In a fourth example of the method optionally including one or more of the first through third examples, the method further comprises displaying, to the user via the client device, a clinical queue comprising a list of individuals prioritized for healthcare intervention based on a plurality of risk scores generated with a plurality of predictive models, wherein receiving the selection of the patient comprises receiving a selection by the user of the patient from the clinical queue. In a fifth example of the method optionally including one or more of the first through fourth examples, the method further comprises retrieving a prediction or risk score from a predictive model of the plurality of predictive models, wherein the prediction or the risk score is responsible for inclusion of the patient in the clinical queue, and adjusting the order of the display modules according to the prediction or the risk score. In a sixth example of the method optionally including one or more of the first through fifth examples of the method, the method further comprises receiving, from the client device, feedback regarding the order of the display modules, and training a predictive model for determining the order with the feedback. In a seventh example of the method optionally including one or more of the first through sixth examples of the method, the plurality of display modules includes one or more of a display module depicting healthcare timelines, a display module depicting future clinical predictions, a display module depicting medical claims history in a textual format, a display module depicting medical claims history in a timeline format, a display module depicting a timeline of pharmaceutical prescriptions, a display module depicting healthcare insurance eligibility, a display module depicting contact information for the patient, and a display module depicting notes relating to the patient provided by a healthcare provider. In an eighth example of the method optionally including one or more of the first through seventh examples, the method further comprises retrieving the information relating to the patient from a plurality of databases stored in separate computing systems, and populating one or more display modules of the plurality of display modules with the information.

In another embodiment, a computer-readable storage medium includes an executable program stored thereon, the program configured to cause a computer processor to receive, from a user of a client device, a selection of a patient, determine, with a predictive model, an order of a plurality of display modules, each display module displaying information relating to the patient, generate a dashboard including the plurality of display modules displayed in the order, transmit the dashboard to the client device for display to the user, receive, from the client device, feedback regarding the order of the plurality of display modules, and update the predictive model with the feedback.

In a first example of the computer-readable storage medium, the program is further configured to predict, with the predictive model for each display module of the plurality of display modules, an actionability or relevancy of each display module for display to the user, and determine the order according to the predicted actionability or relevancy. In a second example of the computer-readable storage medium optionally including the first example, the order comprises a hierarchy of relevance for display to the user such that a display module with a higher predicted actionability or relevancy is displayed prominently in the dashboard while a display module with a lower predicted actionability or relevancy is displayed less prominently in the dashboard. In a third example of the computer-readable storage medium optionally including one or more of the first and second examples, the program is further configured to cause the computer processor to retrieve a risk score for the patient generated by a predictive model trained to calculate the risk score according to medical claims of the patient, and adjusting the order of the display modules according to the prediction or the risk score, wherein the risk score comprises one or more of a prediction of future healthcare costs, a prediction of a length of an in-patient stay, and a prediction of a risk for healthcare episodes.

In yet another embodiment, a system comprises a client device configured for a user, and a server communicatively coupled to the client device and configured with executable instructions in non-transitory memory of the server that when executed cause a processor of the server to: receive, from the client device, a selection of a patient by the user; determine an order of a plurality of display modules, each display module displaying information relating to the patient; generate a dashboard including the plurality of display modules arranged in the order; and transmit the dashboard to the client device for display to the user.

In a first example of the system, the server is further configured with executable instructions in the non-transitory memory that when executed cause the processor to predict, for each display module of the plurality of display modules, an actionability or relevancy of each display module for display to the user, and determine the order according to the predicted actionability or relevancy. In a second example of the system optionally including the first example, the server is further configured with executable instructions in the non-transitory memory that when executed cause the processor to adjust the order of the plurality of display modules based on a type of user for the user. In a third example of the system optionally including one or more of the first and second examples, the server is further configured with executable instructions in the non-transitory memory that when executed cause the processor to adjust the order of the plurality of display modules according to one or more healthcare predictions for the patient. In a fourth example of the system optionally including one or more of the first through third examples, the server is further configured with executable instructions in the non-transitory memory that when executed cause the processor to: generate, with a plurality of predictive models, a plurality of risk scores for a plurality of individuals; construct a clinical queue comprising a list of the plurality of individuals prioritized for healthcare intervention based on the plurality of risk scores; and transmit the clinical queue to the client device for display to the user, wherein the patient is selected by the user from the clinical queue. In a fifth example of the system optionally including one or more of the first through fourth examples, the server is further configured with executable instructions in the non-transitory memory that when executed cause the processor to receive, from the client device, feedback input to the client device by the user regarding the order of the display modules, and train, based on the feedback, a predictive model for determining the order of the plurality of display modules.

In one representation, a method comprises generating, with a plurality of predictive models, a plurality of risk scores for each individual a plurality of individuals based on medical claims of each individual, transmitting a clinical queue to a client device associated with a healthcare provider, the clinical queue comprising a list of individuals prioritized for healthcare intervention based on the plurality of risk scores, receiving feedback from the client device regarding the clinical queue, and updating at least one predictive model of the plurality of predictive models based on the feedback.

In a first example of the method, the method further comprises selectively sorting a list of the plurality of individuals according to one or more risk scores of the plurality of risk scores for each individual, wherein the clinical queue comprises at least a portion of the sorted list. In a second example of the method, the plurality of risk scores comprises one or more of a prediction of future healthcare costs, a prediction of a length of an in-patient stay, and a prediction of a risk for healthcare episodes. In a third example of the method, each predictive model of the plurality of predictive models comprises a machine learning model trained to calculate a risk score for each individual according to the medical claims of each individual. In a fourth example of the method, updating at least one predictive model of the plurality of predictive models based on the feedback comprises training the at least one predictive model with the feedback. In a fifth example of the method, the feedback comprises one or more of an indication of whether a case is opened for an individual, a review of quality of a recommendation of the individual in the clinical queue, and an indication of whether the individual in the clinical queue was reviewed.

In another representation, a computer-readable storage medium includes an executable program stored thereon, the program configured to cause a computer processor to: generate, with a plurality of predictive models, a plurality of risk scores for each individual a plurality of individuals based on medical claims of each individual; transmit a clinical queue to a client device associated with a healthcare provider, the clinical queue comprising a list of individuals prioritized for healthcare intervention based on the plurality of risk scores; receive feedback from the client device regarding the clinical queue; and update at least one predictive model of the plurality of predictive models based on the feedback.

In a first example of the computer-readable storage medium, the executable program is further configured to cause a computer processor to selectively sort a list of the plurality of individuals according to one or more risk scores of the plurality of risk scores for each individual, wherein the clinical queue comprises at least a portion of the sorted list. In a second example of the computer-readable storage medium optionally including the first example, the plurality of risk scores comprises one or more of a prediction of future healthcare costs, a prediction of a length of an in-patient stay, and a prediction of a risk for healthcare episodes. In a third example of the computer-readable storage medium optionally including one or more of the first and second examples, each predictive model of the plurality of predictive models comprises a machine learning model trained to calculate a risk score for each individual according to the medical claims of each individual. In a fourth example of the computer-readable storage medium optionally including one or more of the first through third examples, the executable program is further configured to cause the cause the computer processor to train the at least one predictive model with the feedback to update the at least one predictive model.

In yet another representation, a system comprises a client device configured for a user, and a server, communicatively coupled to the client device via a network, the server configured with executable instructions in non-transitory memory of the server that when executed cause a processor of the server to: generate, with a plurality of predictive models stored in the non-transitory memory, a plurality of risk scores for each individual a plurality of individuals based on medical claims of each individual; transmit, to the client device, a clinical queue comprising a list of individuals prioritized for healthcare intervention based on the plurality of risk scores; receive, from the client device, feedback regarding the clinical queue; and update at least one predictive model of the plurality of predictive models based on the feedback.

In a first example of the system, the server is further configured with executable instructions in the non-transitory memory that when executed cause the processor to: selectively sort a list of the plurality of individuals according to one or more risk scores of the plurality of risk scores for each individual, wherein the clinical queue comprises at least a portion of the sorted list. In a second example of the system optionally including the first example, the plurality of risk scores comprises one or more of a prediction of future healthcare costs, a prediction of a length of an in-patient stay, and a prediction of a risk for healthcare episodes. In a third example of the system optionally including one or more of the first and second examples, each predictive model of the plurality of predictive models comprises a machine learning model trained to calculate a risk score for each individual according to the medical claims of each individual. In a fourth example of the system optionally including one or more of the first through third examples, the server is further configured with executable instructions in the non-transitory memory that when executed cause the processor to train the at least one predictive model with the feedback to update the at least one predictive model. In a fifth example of the system optionally including one or more of the first through fourth examples, the feedback comprises one or more of an indication of whether a case is opened for an individual, a review of quality of a recommendation of the individual in the clinical queue, and an indication of whether the individual in the clinical queue was reviewed. In a sixth example of the system optionally including one or more of the first through fifth examples, the client device comprises a display subsystem, and wherein the client device is configured with executable instructions in non-transitory memory of the client device that when executed cause a processor of the client device to display, to the user via the display subsystem, a graphical user interface depicting the clinical queue. In a seventh example of the system optionally including one or more of the first through sixth examples, the client device further comprises a user interface subsystem configured receive the feedback regarding the clinical queue from the user, and wherein the client device is further configured with executable instructions in the non-transitory memory of the client device that when executed cause the processor of the client device to transmit, via the network, the feedback regarding the clinical queue to the server. In an eighth example of the system optionally including one or more of the first through seventh examples of the system, the server is further configured with executable instructions in the non-transitory memory that when executed cause the processor to generate the clinical queue based on one or more of a geographical region, a healthcare facility, and a healthcare provider associated with the client device.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method comprising:
   collecting medical claims from one or more healthcare databases, each of the medical claims associated with a patient;
   generating a clinical prediction for the patient, using a machine learning model, based on the medical claims associated with the patient;
   receiving, from a user of a client device, a selection of the patient;
   determining an order of a plurality of display modules automatically based on the clinical prediction, wherein each display module displays information relating to the patient, and wherein determining the order of the plurality of display modules includes determining a positioning of the plurality of display modules relative to one another;
   generating a dashboard including the plurality of display modules displayed in the order determined;
   transmitting the dashboard to the client device for display to the user;
   receiving, from the client device, feedback regarding the order of the plurality of display modules; and
   training the machine learning model based on the feedback.

2. The method of claim 1, the method further comprising:
   retrieving user preferences from a user profile of the user; and
   adjusting the order of the plurality of display modules based on the user preferences.

3. The method of claim 1, wherein the plurality of display modules includes a visual timeline of the clinical prediction for the patient.

4. The method of claim 1, wherein the clinical prediction comprises a predicted measure of healthcare consumption.

5. The method of claim 1, the method further comprising:
   receiving, from the client device, feedback regarding the clinical prediction; and training the machine learning model based on the feedback.

6. The method of claim 1, the method further comprising:
   adjusting content of one or more display modules of the plurality of display modules based on the clinical prediction.

7. The method of claim 6, wherein adjusting content of one or more display modules of the plurality of display modules based on the clinical prediction comprises:
   adjusting the display of a medical claims history to emphasize medical claims relating to the clinical prediction.

8. The method of claim 1, wherein determining the order of the plurality of display modules based on the clinical prediction comprises:
   displaying along a top of the dashboard one or more medical claims from a medical claims history, wherein the one or more medical claims pertain to the clinical prediction.

9. The method of claim 1, wherein the order is a descending order where more actionable display modules of the plurality of display modules are displayed near a top of the dashboard while less actionable display modules are displayed near a bottom of the dashboard.

10. A method, comprising:
    collecting patient data from one or more databases, wherein the patient data is associated with a patient;
    generating one or more clinical predictions for the patient, using at least a first machine learning model, based on the patient data;
    receiving, from a user of a client device, a selection of the patient;
    predicting with a second machine learning model an actionability for each display module of a plurality of display modules based on the patient data and a user profile of the user, wherein the plurality of display modules includes a display module comprising a visual timeline of the one or more clinical predictions for the patient;
    determining an order of the plurality of display modules automatically based on the actionability for each display module of the plurality of display modules, wherein determining the order of the plurality of display modules includes determining a positioning of the plurality of display modules relative to one another;
    generating a dashboard including the plurality of display modules displayed in the order determined;
    transmitting the dashboard to the client device for display to the user;
    receiving, from the client device, feedback regarding the order of the plurality of display modules; and
    training the first machine learning model based on the feedback.

11. The method of claim 10, the method further comprising:
    adjusting the order of the plurality of display modules based on the one or more clinical predictions.

12. The method of claim 11, wherein adjusting the order of the plurality of display modules based on the one or more clinical predictions comprises:
    positioning a first display module of the plurality of display modules along a top of the dashboard, and positioning a second display module of the plurality of display modules below the first display module based on relevancy of the first display module and the second display module to the one or more clinical predictions.

13. The method of claim 10, wherein the one or more clinical predictions includes a first clinical prediction generated by the first machine learning model, and a second clinical prediction generated by a third machine learning model; and wherein the visual timeline of the one or more clinical predictions for the patient includes the first clinical prediction and the second clinical prediction.

14. The method of claim 10, the method further comprising:
    retrieving a user type from a user profile of the user, wherein the user type is one of a medical doctor (MD), a physician assistant (PA), a certified nursing assistant (CNA), a nurse practitioner (NP), a doctor of osteopathic medicine (DO), a registered nurse (RN), a licensed practical nurse (LPN), an administrative assistant, and an insurance administrator; and
    adjusting the order of the plurality of display modules based on the user type.

15. The method of claim 10, the method further comprising:
    displaying, to the user via the client device, a clinical queue comprising a list of individuals prioritized for healthcare intervention based on the one or more clinical predictions generated by at least the first machine learning model, wherein receiving the selection of the patient comprises receiving a selection by the user of the patient from the clinical queue.

16. The method of claim 10, wherein the plurality of display modules includes a visual timeline of future cost predictions for the patient.

17. A computer-readable storage medium including an executable program stored thereon, the program configured to cause a computer processor to:
- collect patient data associated with a patient from one or more databases;
- generate a first patient care prediction for the patient, using a first machine learning model, based on the patient data;
- generate a second patient care prediction for the patient, using a second machine learning model, based on the patient data;
- receive, from a user of a client device, a selection of the patient;
- predict with a third machine learning model an actionability for each display module of a plurality of display modules based on the patient data and a user profile of the user;
- determine an order of the plurality of display modules automatically based on the actionability for each display module of the plurality of display modules, wherein determining the order of the plurality of display modules includes determining a positioning of the plurality of display modules relative to one another;
- adjust the order of the plurality of display modules based on the first patient care prediction and the second patient care prediction;
- generate a dashboard including the plurality of display modules displayed in the adjusted order;
- transmit the dashboard to the client device for display to the user;
- receive, from the client device, feedback regarding the adjusted order of the plurality of display modules; and
- train the third machine learning model based on the feedback.

18. The computer-readable storage medium of claim 17, wherein the program is further configured to cause the computer processor to:
- receive, from the client device, feedback regarding the order of the plurality of display modules; and
- train the third machine learning model based on the feedback.

19. The computer-readable storage medium of claim 17, wherein the program is configured to adjust the order of the plurality of display modules based on the first patient care prediction and the second patient care prediction by:
- positioning a display module of the plurality of display modules along a top of the dashboard based on the first patient care prediction and the second patient care prediction.

20. The computer-readable storage medium of claim 17, wherein the program is further configured to cause the computer processor to adjust content of one or more display modules of the plurality of display modules based on one or both of the first patient care prediction and the second patient care prediction.

* * * * *